United States Patent [19]

Elliott et al.

[11] Patent Number: 5,042,985
[45] Date of Patent: Aug. 27, 1991

[54] DILATATION CATHETER SUITABLE FOR PERIPHERAL ARTERIES

[75] Inventors: Sandra L. Elliott, Sunnyvale; Jeffrey L. Kraus, San Jose; Craig E. Mar, Sunnyvale, all of Calif.

[73] Assignee: Advanced Cardiovascular Systems, Inc., Santa Clara, Calif.

[21] Appl. No.: 350,276

[22] Filed: May 11, 1989

[51] Int. Cl.⁵ ............................................. A61M 29/02
[52] U.S. Cl. ..................... 606/192; 600/18; 604/96; 606/194
[58] Field of Search ............... 606/191, 192, 194, 195, 606/196; 604/103, 96; 600/18

[56] References Cited

U.S. PATENT DOCUMENTS

| | | | |
|---|---|---|---|
| 4,276,874 | 7/1981 | Wolvek et al. | 600/18 |
| 4,362,150 | 12/1982 | Lombardi, Jr. et al. | 600/18 |
| 4,641,654 | 2/1987 | Sampson et al. | 606/192 |
| 4,821,722 | 4/1989 | Miller et al. | 606/192 |
| 4,838,268 | 6/1989 | Keith et al. | 606/194 |

Primary Examiner—Steven A. Bratlie
Attorney, Agent, or Firm—Fulwider, Patton, Lee & Utecht

[57] ABSTRACT

A steerable balloon dilatation catheter which is particularly suitable for peripheral arteries having an elongated tubular member with a flexible, inelastic balloon on the distal end. The tubular member has a relatively stiff proximal portion formed of stainless steel and a relatively flexible distal portion formed of a polyester. A fixed guiding member is disposed within the catheter bonded to the proximal portion of the tubular member, to a short relatively rigid cylindrical member bonded to the distal portion of the tubular member and the distal end of the balloon.

12 Claims, 1 Drawing Sheet

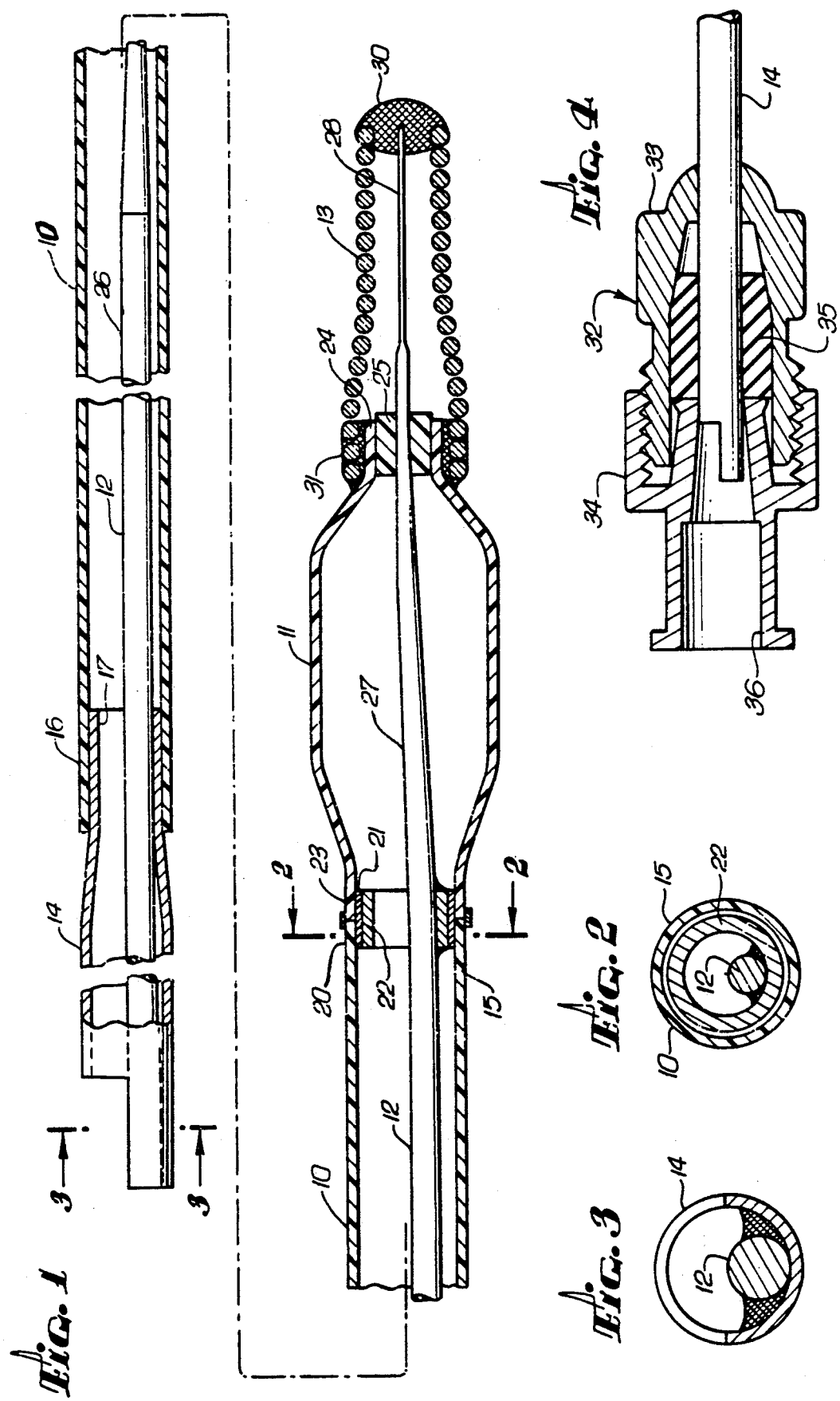

DILATATION CATHETER SUITABLE FOR PERIPHERAL ARTERIES

BACKGROUND OF THE INVENTION

This invention is related to a balloon dilation catheter for angioplasty procedures, particularly in peripheral arteries.

Angioplasty procedures generally involve advancing a dilatation catheter with an inflatable inelastic balloon on the distal portion through a patient's vasculature until the balloon crosses a stenotic region. Inflation fluid is introduced into an inner lumen of the catheter at the proximal end thereof to inflate the balloon and thereby dilate the stenosis. Usually, a guidewire is first advanced through the patient's arteries until the distal tip thereof passes through the stenotic region. The dilatation catheter is then advanced over the guidewire until the balloon is in its proper position for stenotic dilatation. This procedure is used both in coronary arteries and in peripheral arteries. The former is called percutaneous transluminal coronary angioplasty (PTCA) and the latter merely percutaneous transluminal angioplasty (PTA).

Dilatation catheter for angioplasty procedures with fixed guidewires or guiding elements have been used with greater frequency because such catheters generally have lower profiles and have better pushing characteristics which facilitate advancing through the patient's vasculature.

Further details of dilatation catheters, guidewires and associated accessories for angioplasty procedures are described in the following U. S. Patents which are incorporated herein in their entirety.

| | | | |
|---|---|---|---|
| 4,323,071 | Simpson-Robert | 4,538,622 | Samson et al. |
| 4,332,254 | Lundquist | | |
| 4,439,185 | Lundquist | 4,554,929 | Samson et al. |
| 4,468,224 | Enzmann et al. | 4,582,181 | Samson |
| 4,516,972 | Samson | 4,616,652 | Simpson |
| 4,538,622 | Samson et al. | 4,619,263 | Frisbie et al. |
| 4,619,274 | Morrison | 4,641,654 | Samson et al. |
| 4,664,113 | Frisbie et al. | 4,721,117 | Mar et al. |

While the dilatation catheters and guidewires for peripheral arteries are very similar to dilatation catheters for coronary arteries, there are significant differences due to the nature of the arteries being treated. Generally, the catheters for peripheral arteries have much larger diameters and have a greater degree of pushability than catheters for coronary use. Additionally, for example, only a small distal portion, i.e., the last 30 cm, of a dilatation catheter for coronary arteries will pass through tortuous arterial passageways whereas most of a dilatation catheter for peripheral arteries will pass through tortuous passageways. Thus the catheter and guidewire for peripheral artery use needs to be longitudinally flexible over essentially the entire length thereof which is introduced into the patient. However, increasing the longitudinal flexibility usually entails a loss in the pushability of the catheter. What has been needed is a dilatation catheter with enhanced flexibility and pushability to more readily be advanced through severe tortuous arterial passageways. The present invention satisfies that need.

SUMMARY OF THE INVENTION

This invention is directed to a dilatation catheter for angioplasty procedures, particularly for peripheral arteries.

The dilatation catheter of the invention generally comprises a main tubular member having an inner lumen extending therein, an inflatable, inelastic balloon on the distal portion of the tubular member, and a guiding member extending through the inner lumen of the tubular member, through the interior of the balloon and out the distal end thereof. A flexible body such as a helical coil is disposed about the portion of the guiding element which extends out of the distal end of the balloon and has a rounded plug on the distal tip thereof.

The main tubular member generally has a proximal portion which is relatively stiff and is preferably formed of hypotubing and a distal portion which is relatively flexible and is preferably formed of high strength thermoplastic elastomers such as polyesters. The length of the flexible distal portion generally comprises from about 50 to about 85 percent of the length of the catheter.

The distal portion of the tubular member is provided with a short relatively rigid tubular element in the interior thereof which is preferably hypotubing. The guiding element extending therethrough is bonded to the interior of the short tubular element by means such as soldering, brazing or welding. Soldering with gold is preferred.

The flexible body mounted about the portion of the guiding member which extends out the distal end of the balloon is preferably a helical coil formed at least in part of a radiopaque material, such as platinum, palladium, molybdenum, tungsten, rhenium, and alloys thereof. Advancement of the catheter is greatly enhanced if the coil tapers distally toward the rounded plug on the distal tip thereof.

The guiding element generally extends from the proximal end of the tubular member to the distal tip of the coil and is preferably formed of suitable stainless steel. The distal portion is tapered to increase the flexibility thereof, and the distal extremity thereof, which is secured to the rounded plug, is preferably flattened. The proximal end of the guiding member is secured by suitable means such as soldering, brazing, or welding to the proximal portion of the main tubular member.

The inflatable balloon member on the distal end of the catheter is relatively inelastic so that it will inflate to a predetermined size and expand very little even when inflated to high internal pressures. Suitable balloon materials include thermoplastic elastomers, such as polyethylene and polyethylene terephthalate. Both of these plastics can be formed into balloons having a high degree of biaxial orientation which provides the desired strength and elongation characteristics.

The catheter of the invention has excellent flexibility and pushability and can be advanced deep within a patient's tortuous peripheral arterial system. Moreover, there is little tendency for the plastic members to stretch when the catheter is removed from a patient because the guide member is secured to the proximal portion of the tubular member, to the short cylindrical member and to the distal end of the balloon. These and other advantages of the invention will become more apparent from the following detailed description thereof when taken in conjunction with the accompanying exemplary drawings.

BRIEF DESCRIPTION OF THE DRAWINGS

FIG. 1 is an elevational view, partially in section, of a dilatation catheter which embodies features of the invention;

FIG. 2 is a transverse cross-sectional view taken along the lines 2—2 shown in FIG. 1;

FIG. 3 is a transverse cross-sectional view taken along the lines 3—3 shown in FIG. 1; and FIG. 4 is an elevational view, partially in section of a Touhy Borst adapter mounted on the proximal end of the catheter shown in FIG. 1.

DETAILED DESCRIPTION OF THE INVENTION

FIGS. 1-3 illustrate a dilatation catheter which embodies features of the invention. Generally, the catheter includes a main tubular member 10, an inflatable balloon 11 on the distal portion of the tubular member, an inner guide member 12 which extends through the tubular member and the interior of the balloon, and a helical coil 13 which is disposed about a portion of the guide member which extends out the distal end of the balloon.

The main tubular member has a relatively stiff proximal portion 14, which is preferably formed of stainless steel hypotubing, and a longitudinally flexible distal portion 15, which is preferably formed of a high-strength polymeric plastic, such as a polyester. The proximal end 16 of the distal portion 15 is fitted over and secured to the tapered distal end 17 of the proximal portion 14. The interfitting ends 16 and 17 may be bonded by an adhesive or other suitable means.

The distal extremity 20 of the distal portion 15 is bonded by an adhesive 21 or other suitable means to a short, diametrically rigid cylindrical member 22, preferably stainless steel hypotubing, which partially fits therein. The proximal skirt 23 of the balloon 11 is bonded to the distal portion of the cylindrical member 22. The distal skirt 24 of the balloon 11 is bonded by adhesive 25 to the guide member 12 which extends therethrough.

The guide member 12 generally has a main wire section 26 of constant diameter, one or more tapered portions 27, and a flattened distal section 28. Rounded plug 30 is formed on the distal tip of flattened section 28. The proximal end of the main wire section 26 is secured to the interior of the proximal portion 14 by suitable means, such as soldering, brazing, or welding. The guide member 12 is also bonded at an intermediate location, such as the tapered section 27 to the interior of the cylindrical member 22.

Helical coil 13, preferably tapered as shown in FIG. 1 to facilitate advancement of the catheter through tortuous anatomy, is bonded at the proximal end thereof to the exterior of the distal skirt 24 of the balloon 11 by a suitable adhesive 31 and the distal end is bonded to the rounded plug by welding or the like.

As shown in FIG. 4, the proximal end of the tubular member 10 is secured to a Touhy Borst adapter 32 which has a body 33, preferably formed of polyvinyl chloride, a cap 34, preferably formed of nylon, and an inner seal member 35, preferably formed of silicone. The cap 34 has a female Luer 36 connection which is adapted to receive an inflation device (not shown) such as the Indeflator ™ inflation device sold by Advanced Cardiovascular Systems, Inc., assignee of the present application. See U.S. Pat. No. 4,439,185 and U.S. Pat. No. 4,743,230.

The proximal portion 14 of the main tubular member 10 typically has a length of about 50 cm, an outer diameter of about 0.032 inch and an inner diameter of about 0.023 inch. The distal end thereof is ground to an outer diameter of about 0.027 inch to fit within the proximal end of the distal portion 15 of the tubular member 10. The distal portion 15 is typically about 95 cm in length and has an outer diameter of about 0.034 inch and an inner diameter of about 0.028 inch. The short cylindrical member 22 has a length of about 5 mm, an outer diameter of about 0.027 and an inner diameter of about 0.023 inch. The main wire section 26 of the guide member 12 is about 125 cm in length and has an outer diameter of about 0.012 inch. The tapered section 27 is about 12 cm in length with the flattened distal end thereof being about 2 cm long and about 0.002 inch thick. The coil 13 tapers from an outer diameter of about 0.034 inch at the proximal end to 0.018 inch at the plug 30. The balloon 11 including the skirts 23 and 24 is about 3 cm long and can have various inflated diameters as is well known in the art, typically ranging from about 1 to about 5 mm.

The proximal portion 14, the short cylindrical section 22 and the guide member 12 generally can be made from stainless steel in a conventional manner, although all or portions thereof may be made from other materials such as nitinol, which is an alloy of nickel and titanium having super elastic properties.

The distal portion 15 of the main tubular member 10 is preferably formed of a polyester elastomer preferably a block copolymer of polybutylene terephthalate such as Hytrel ™ 7246. Hytrel is a registered trademark of DuPont.

The balloon is preferably formed of an inelastic thermoplastic material, such as polyethylene and polyethylene terephthalate, in a conventional manner well known in the art to generate a biaxial orientation. Polyvinyl chloride may also be used.

While the present invention is described herein with reference to an embodiment which is particularly adapted for use in peripheral arteries, various modifications can be made without departing from the scope thereof.

What is claimed is:

1. A dilatation catheter having a fixed guiding member therein for angioplasty procedures, comprising:
   a) an elongated tubular member having an inner lumen extending therein, a relatively stiff proximal portion and relatively flexible distal portion;
   b) a short diametrically rigid cylindrical element disposed at least in part within the inner lumen in the distal portion of the tubular member and secured thereto;
   c) a flexible inelastic inflatable balloon member secured to the distal end of the elongated tubular member;
   d) a guiding member extending through the interiors of the tubular member and the flexible balloon member and having a portion extending out the distal end of the balloon member, the guiding member being bonded to the proximal portion of the tubular member within the inner lumen extending therein and to the cylindrical element disposed within the distal portion of the tubular member, and the distal end of the balloon being secured about the guiding member; and e) a flexible body disposed about the portion of the guiding member extending out of the distal end of the balloon member and secured thereto.

2. The dilatation catheter of claim 1 wherein the flexible body disposed about the guiding member is a helical coil.

3. The dilatation catheter of claim 2 wherein the coil tapers in the distal direction.

4. The dilatation catheter of claim 1 wherein the proximal portion of the tubular member is formed of hypotubing.

5. The dilatation catheter of claim 4 wherein the distal portion of the tubular member is formed of high strength plastic.

6. The dilatation catheter of claim 5 wherein the high strength plastic material is thermoplastic polyester elastomer.

7. The dilatation catheter of claim 6 wherein the polyester is a copolymer of polybutylene terephthalate and polyether glycol.

8. The dilatation catheter of claim 1 wherein the distal portion of the balloon has a skirt which is bonded to the guiding member passing therethrough.

9. The dilatation catheter of claim 1 wherein the balloon is formed of a thermoplastic material selected from the group consisting of polyethylene and polyethylene terephthalate.

10. The dilatation catheter of claim 1 wherein the guiding member extends to a rounded plug at the distal tip of the flexible member.

11. The dilatation catheter of claim 1 wherein the length of the distal portion of the tubular member ranges from about 50 to about 85 percent of the length of the tubular member.

12. The dilatation catheter of claim 1 wherein the short cylindrical element is formed of stainless steel hypotubing.

* * * * *